(12) United States Patent
Gordon

(10) Patent No.: US 6,593,143 B1
(45) Date of Patent: Jul. 15, 2003

(54) CENTRIFUGE SYSTEM WITH CONTACTLESS REGULATION OF CHEMICAL-SAMPLE TEMPERATURE USING EDDY CURRENTS

(75) Inventor: Gary B. Gordon, Saratoga, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 295 days.

(21) Appl. No.: 09/614,534

(22) Filed: Jul. 11, 2000

Related U.S. Application Data

(63) Continuation-in-part of application No. 09/576,690, filed on May 23, 2000, now Pat. No. 6,491,805, and a continuation-in-part of application No. 09/514,975, filed on Feb. 29, 2000, now Pat. No. 6,309,875.

(51) Int. Cl.[7] ................. G01N 35/00; G01N 9/30; B04B 15/02; B04B 5/02
(52) U.S. Cl. ................. 436/45; 422/64; 422/72; 436/86; 436/89; 436/165; 436/174; 494/13; 494/14; 494/84; 494/16; 494/19
(58) Field of Search ................. 422/64, 72; 435/41, 435/287.2, 283.1, 280.7, 288.3; 436/45, 86, 89, 165, 174; 494/14, 19, 16, 81, 84, 13

(56) References Cited

U.S. PATENT DOCUMENTS

| | | | |
|---|---|---|---|
| 3,848,796 A | * 11/1974 | Bull | |
| 3,912,799 A | * 10/1975 | Chisholm | |
| 4,456,581 A | * 6/1984 | Edelmann et al. | 422/72 |
| 4,498,896 A | * 2/1985 | Leis | 494/14 |
| 4,776,832 A | 10/1988 | Martin et al. | 494/19 |
| 4,814,282 A | 3/1989 | Holen et al. | 436/165 |
| 4,898,832 A | * 2/1990 | Klose et al. | 436/45 |
| 5,077,013 A | * 12/1991 | Guigan | 422/64 |
| 5,089,417 A | 2/1992 | Wogoman | 436/45 |
| 5,232,667 A | * 8/1993 | Heib et al. | 422/82.04 |
| 5,773,238 A | * 6/1998 | Shukla | 435/41 |
| 6,153,012 A | * 11/2000 | Rupp et al. | 118/715 |
| 6,309,875 B1 | * 10/2001 | Gordon | 435/287.2 |
| 6,348,176 B1 | * 2/2002 | Hammer et al. | 422/64 |
| 6,361,486 B1 | * 3/2002 | Gordon | 494/19 |

OTHER PUBLICATIONS

R. Watson Chem. Abstr. 1990, 112, abstract 193190z.*

* cited by examiner

Primary Examiner—Arlen Soderquist

(57) ABSTRACT

A coaxial-drive centrifuge provides for contactless regulation of sample temperature. The sample is contained in a multi-station chemical-processing circuit that has a metal receptor at each station. On demand, a stationary inductor induces eddy currents in the receptor as it spins by. Dissipation of the eddy current heats the receptor and the surrounding sample. The receptor has a thermal sensor that provides an optical indication of the sample temperature. A stationary contactless reader reads the optical indication. A controller activates the inductor when the reading indicates an actual temperature below a predetermined target temperature. When heating is required, the inductor is pulsed as the receptor is aligned with a gap in the inductor.

The chemical-processing circuit is designed for a specific series of chemical reactions, in this case, a polymerase chain reaction (PCR) is implement as an iterated series of three steps. To this end, the chemical-processing circuit has three stations arranged in a closed loop with interconnecting channels. When a treatment is completed, the chemical-processing circuit tilts so that the sample to the next station for the next treatment. Each station has its own receptor and thermo-sensor so that each treatment can be performed at its respective optimal temperature. The centrifuge system thus provides for automating a sequence of chemical processes using contactless regulation of temperature.

16 Claims, 4 Drawing Sheets

CENTRIFUGE SYSTEM WITH CONTACTLESS REGULATION OF CHEMICAL-SAMPLE TEMPERATURE USING EDDY CURRENTS

This is a continuation-in-part application of U.S. patent application Ser. No. 09/514,975, filed Feb. 29, 2000, now U.S Pat. No. 6,309,875, and a continuation-in-part application of U.S. patent application Ser. No. 09/576,690, filed May 23, 2000, now U.S. Pat. No. 6,491,804.

BACKGROUND OF THE INVENTION

The present invention relates to analytical chemistry and, more particularly, to centrifuge-based automated sample treatment systems. A major objective of the present invention is to provide rapid and fine temperature control during a series of sample treatments in a centrifuge-induced supergravity field.

The standard of living in modern societies has been greatly enhanced by advances in chemical, biological, and medical sciences. These fields all involve the separation of samples into constituent components that may then be processed to aid in their identification and/or quantification. The centrifuge is an important instance of instrumentation used to separate sample components.

A simple centrifuge has a centrifuge rotor that is spun, e.g., by a motor. Typically, a liquid chemical sample spins with the rotor. The spinning liquid sample components are subjected to a centrifugal force ($F=m\omega^2 r$) proportional to their mass, their distance from the centrifuge spin axis, and the square of the spin rate. The effect of the centrifugal force is much like the effect of gravity-liquid components are separated according to their relative densities. However, unlike gravity, the centrifugal force is readily controlled, e.g., by controlling the spin rate. Thus, a centrifuge can generate centrifugal forces orders of magnitude greater than gravity at the earth's surface. Generally, the "supergravity" conditions of a centrifuge are much more effective than gravity in separating sample components.

In addition, the supergravity conditions afforded by a centrifuge can be used to overcome liquid surface effects that might otherwise impede sample movement. Accordingly, centrifuges that can control the tilt of a chemical-processing unit relative to the centrifugal force can be used for pouring, mixing, filtering, and facilitating chemical reactions. Furthermore, tilting can be used to control liquid movement among multiple processing stations of a chemical-processing circuit so that a series of processes can be implemented without manual intervention. Thus, a centrifuge with tilt control can automate sample processing conventionally performed manually by chemists.

Independent control of centrifuge spin rate and tilt action is disclosed in U.S. Pat. No. 4,814,282 to Holen et al. Tilt of a chemical-processing circuit is used to transfer liquid from one station to another under the influence of centrifugal force. A tilt-drive assembly, including motor and drive chain, is attached to the centrifuge rotor so that it rotates therewith. Power is delivered to the tilt-drive motor via slip rings, which tend to wear out as they are not generally designed to operate at centrifuge speeds. In this approach, any sensors used to track tilt would also rotate at high speeds, further complicating operation. In addition, centrifuge forces are applied to the tilt motor and the drive train. For example, a 1-pound motor must withstand 1000-pound forces in a readily achievable 1000 G supergravity field. Thus, there are a number of robustness issues that can only be addressed with additional complexity and expense.

These robustness issues are mitigated in the centrifuge disclosed in U.S. Pat. No. 5,089,417 to Wogoman. In the Wogoman centrifuge, a holder for a chemical-processing circuit snaps from a first tilt orientation to a second tilt orientation when the centrifuge exceeds a predetermined rotation rate. Similarly, the first tilt orientation is resumed when the centrifuge spin rate falls below the threshold rate. Thus by increasing and decreasing the centrifuge spin rate, sample movement between reaction stations of the chemical-processing circuit can be controlled. However, this approach provides little flexibility in selecting the centrifuge spin rate or tilt angles relative to the centrifugal force. It would be preferable to control the centrifuge rotation and the tilt actions independently.

U.S. Pat. No. 4,776,832 to Martin et al. avoids the need for physical connections to drive a tilt rotor by using inductive motors. The inductive motors include induction rotors that are physically coupled to holders, e.g., for reaction cells, and stationary stators, which are located beneath the centrifuge rotor (wheel). The stators induce eddy currents in the induction rotors, causing them to rotate. No physical connection is required between the stators and the induction rotors, eliminating the need to deliver power through slip rings. On the other hand, the non-physical coupling of drive and induction rotor does not ensure precise and flexible control of sample-container orientation relative to the supergravity field.

Parent U.S. patent application Ser. No. 09/576,690 discloses a coaxial-drive centrifuge in which part of the drive assembly for the tilt motion is coaxial with the centrifuge axis. This arrangement overcomes the robustness limitations of Holen et al., the flexibility limitations of Wogoman, and the precision limitations of Martin et al. A tilt-drive motor provides complete control over tilt without restricting centrifuge rotation rates. The tilt-drive motor is stationary, so electrical coupling is not required to a rotating element. The coupling between the tilt-drive motor and the chemical-processing circuit is mechanical, so there is no problem of precision in tilt control.

The coaxial-drive centrifuge holds the promise for rapid and fully automated sample processing through a series of treatment steps. For example, a polymerase chain reaction (PCR) technique requires many iterations of a series of steps. PCR is used to copy small fragments of doxyribonucleic acid (DNA); the procedure can be iterated so that the amount of DNA grows exponentially. Thus, a limitless amount of DNA sample can be "amplified" from a single DNA fragment. This can allow, for example, multiple parallel destructive analyses to be performed. PCR techniques have accelerated the study of gene functions and gene mappings (e.g., in the Human Genome Project). Generally, PCR is useful in biology, clinical medice, and forensic science.

One variant of PCR , begins with heating a DNA solution (e.g., to 90° C.) so that individual strands separate. Then the DNA solution is cooled (e.g., to 50–60° C.), allowing oligonucleotide primers to bind to the separated DNA. Then the temperature is raised (e.g., to 70° C.) so that polymerase can copy the DNA rapidly. These three phases, melting, annealing, and extension, can be iterated so that the amount of DNA grows exponentially. Typically, the DNA sample remains in a container that is heated and cooled by using temperature controlled baths. The time for the temperature to transfer through the sample container wall is a limiting factor in the rate at which the PCR reaction can be iterated.

Tilt-capable centrifuges with multi-chamber chemical-processing circuits could be used so that each PCR step can be conducted in a dedicated station. Each station can be kept at the temperature associated with one step, e.g., melting, annealing, and extension. Changes in container orientation between steps can be used to move the sample from station to station to automate the processing.

However, the promise for rapid and fully automated chemical-sample processing faces a challenge in temperature control. Typically, different temperatures are required for different sample treatments. The entire centrifuge can be temperature controlled, but then it is difficult to change temperatures rapidly. At best, slow temperature changes delay processing throughput; at worst, slow temperature changes can be incompatible with certain treatment requirements. Local resistive heaters can provide rapid heating. However, delivering electrical power to a rotating chemical-processing circuit for heat control faces linkage challenges as discussed above with respect to Holen et al.

Moreover, sample temperature should be monitored to provide precise closed-loop control thereof. Once again, electrical connections to rotating elements are preferably avoided. What is needed is a system that provides for rapid and precise temperature control to a chemical-processing circuit in the context of a centrifuge.

SUMMARY OF THE INVENTION

The present invention provides a centrifuge with inductive temperature control of a tiltable chemical-processing circuit. The centrifuge has a centrifuge rotor, a centrifuge-drive assembly, a chemical-processing unit, a tilt-drive assembly, and an inductor. The tilt-drive assembly is mechanically coupled to the chemical-processing unit to provide for precise and flexible control of tilt relative to the centrifugal force provided by the centrifuge. The chemical-processing unit includes a receptor in which eddy currents are generated when exposed to the alternating magnetic field generated by the inductor. The eddy-current energy is dissipated as heat due to resistance in the receptor.

Energy transfer between the inductor and the receptor is contactless. Accordingly, the inductor can be "stationary" in the sense that it does not rotate with the centrifuge rotor or the chemical-processing circuit. Thus, electrical power can be supplied to the inductor through standard cabling. So that power is not wasted, and more tightly directed to a small zone on the rotor, the alternating magnetic field can be preferably generated only at times that are at least in part a function of the centrifuge rotor orientation.

The chemical-processing unit can include an optical temperature sensor. This can be read by a stationary optical reader as the chemical-processing circuit rotates by. The optical reader can be powered via standard electrical cabling and its signal output can be provided to a controller that regulates the temperature of the sample. The temperature at which the sample is to be maintained depends on the treatment, which can correspond to the station or container location of the sample. Thus, the maintained temperature can be determined as a function of the tilt orientation of the chemical-processing circuit relative to the centrifugal force applied by the centrifuge.

The basic method provided for by the present invention involves spinning a chemical-processing unit about a centrifuge axis so that a centrifugal force is applied to the chemical sample. Movement of the sample within the chemical-processing unit is effected by titling the chemical-processing unit relative to the centrifugal force. Heating of the sample is achieved by inducing eddy currents in the chemical-processing unit using an inductor. Preferably, the inductor generates the eddy currents only when a receptor is aligned with the inductor, as determined by the centrifuge orientation. Regulation of sample temperature can be achieved by contactlessly reading a thermo-sensor included with the chemical-processing unit.

If a chemical-processing circuit (a multi-station chemical-processing unit with channels permitting sample flow between stations) is used, the method of the invention provides for automated processing sequences. The chemical-processing circuit can be oriented relative to the centrifugal force so that the chemical sample is maintained at the first processing station. Once the first treatment is complete, the chemical-processing circuit can be tilted so that the sample flows to a second station for a second treatment.

Where the different treatments require different temperatures, each station can include its own thermo-sensor. The contactless optical reader can read whichever thermo-sensor corresponds to the present location of the sample. A controller can vary inductor pulse widths to control the rate of heating as appropriate to minimize deviations of the actual sample temperature from the target sample temperature.

In a more specific method of the invention, a sample is inserted into a multi-station chemical-processing circuit. Centrifugal force is applied with the chemical-processing circuit oriented so that the sample is held in the first station. In the meantime, the temperature of the sample is regulated using a sensor in the container so that a first temperature is maintained. When the first treatment is completed, the orientation of the chemical-processing circuit relative to the centrifugal force is changed so that the sample moves to the second station. Then the sample is maintained in the second station while the second treatment is applied at a second temperature maintained through regulation response to the sensor.

In the context of PCR, the present invention permits rapid amplification of DNA fragments. For example, each of three stations of a chemical-processing circuit can be dedicated to one of the three phases, melting, annealing, and extension, of the PCR procedure. The chemical-processing circuit can be tilted to pour the DNA sample from station to station. Each station can be kept at the appropriate temperature for the corresponding phase of the PCR procedure. The chemical-processing circuit can be rocked back and forth to agitate the DNA sample to facilitate uniform temperature changes. Thus, the invention provides for rapid automated PCR reactions. Reactions with similar requirements for temperature changes and agitation are similarly facilitated by the present invention.

The present invention provides for rapid and fully automated multi-treatment sample processing with rapid and precise contactless sample temperature control. The chemical-processing circuit is not encumbered either by cables to supply heat or to power a temperature sensor, or to provide feedback to a controller. These and other features and advantages of the invention are apparent from the description below with reference to the following drawings.

BRIEF DESCRIPTION OF THE DRAWINGS

In FIG. 3, signal lines are solid and functional lines are dashed.

DESCRIPTION OF THE PREFERRED EMBODIMENTS

Figure 1:
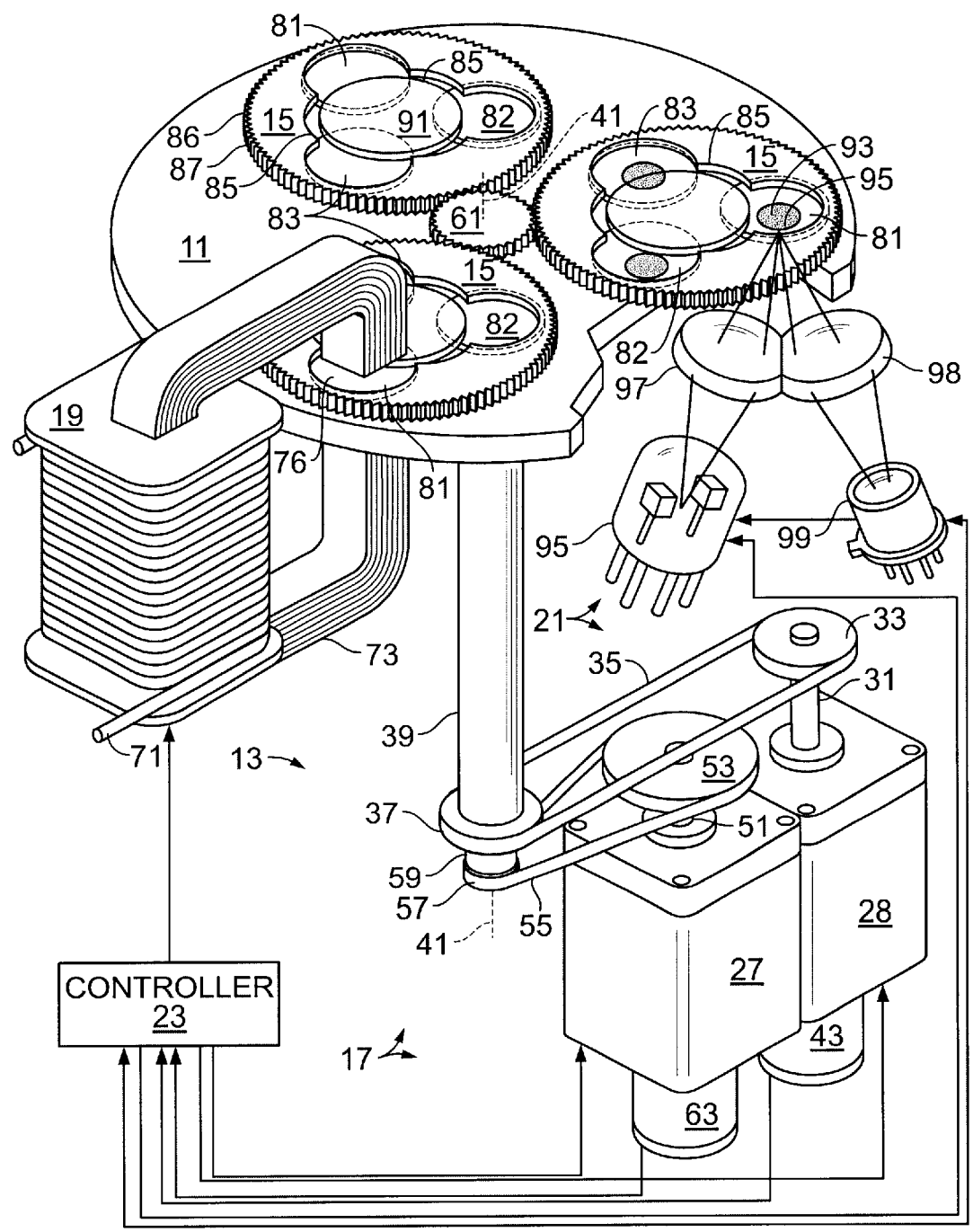
FIG. 1 is a partially isometric schematic view of a centrifuge system in accordance with the present invention.
Figure 2A:
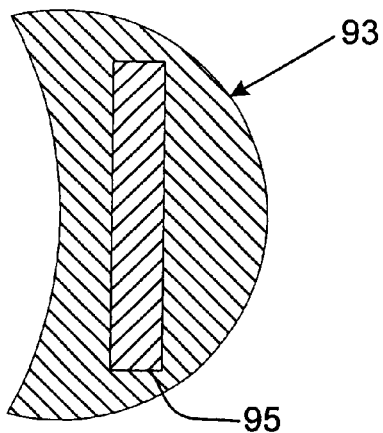
FIGS. 2A, 2B, and 2C are bottom plan views of a chemical-processing circuit (as used in the centrifuge system of FIG. 1) at three different temperatures.
Figure 2B:
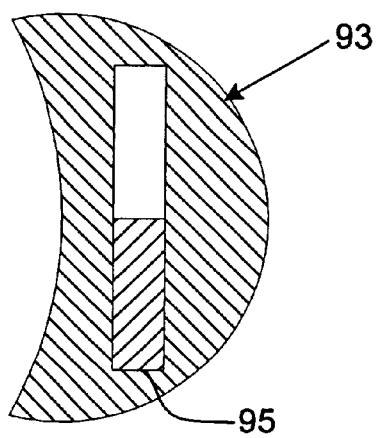
Figure 2C:
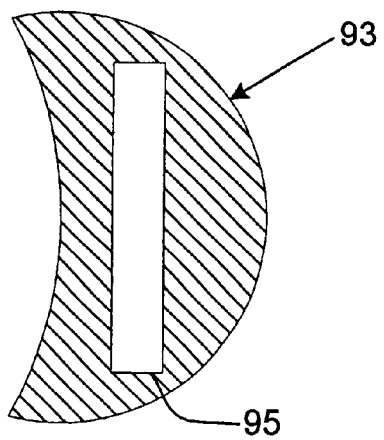

In accordance with the present invention, a centrifuge system AP1 comprises a centrifuge rotor 11, a centrifuge-drive assembly 13, three chemical-processing circuits 15, a tilt-drive assembly 17, an inductor 19, an optical reader 21, and a controller 23 as shown in FIG. 1. Centrifuge drive assembly 13 includes a centrifuge motor 25, and tilt-drive assembly 17 includes a tilt-motor 27, both motors are mounted to a stationary centrifuge housing (not shown). Inductor 19 and optical reader 21 are stationary components fixed to the housing. Inductor 19 provides for contactless heating of chemical-processing circuits 15, while optical reader 21 provides for contactless monitoring of sample temperature.

Centrifuge-drive assembly 13 comprises centrifuge motor 25 that includes a centrifuge-motor shaft 31, a centrifuge-motor pulley 33, a centrifuge drive belt 35, a centrifuge-rotor pulley 37, and a hollow centrifuge shaft 39. Centrifuge rotor 11, centrifuge shaft 39, and centrifuge-rotor pulley 37 rotate together about a centrifuge axis 41. Likewise, centrifuge-motor-pulley 33 is rigidly attached to centrifuge-motor shaft 31 so that they turn together. Pulleys 33 and 37 are geared, as is drive belt 35 that connects them. The gear ratio between pulleys 33 and 37 is 1:1 so that centrifuge rotor 11 turns at the same rate as centrifuge motor shaft 31.

Centrifuge motor 25 includes a position encoder 43 so that the orientation of centrifuge motor shaft 39 can be precisely tracked. This allows the rotation rate of servo-controlled motor 25 to be precisely controlled. In addition, the orientations of centrifuge rotor 11 and centrifuge motor shaft 31 are initialized so that the centrifuge rotor orientation is known from the centrifuge motor-shaft orientation. The centrifuge-motor orientation is used by controller 23 to determine when to activate inductor 19 to heat a sample.

Tilt-drive assembly 17 comprises tilt-drive motor 27 with a tilt-motor shaft 51, a tilt-motor pulley 53, a tilt-drive belt 55, a tilt-shaft pulley 57, a tilt-drive shaft 59, and a tilt-drive pinion 61. Tilt-motor pulley 53 is mounted on tilt-drive motor shaft 51 so that they turn together. Toothed tilt-drive belt 55 links geared pulleys 53 and 57 so that they turn based on a 3:1 ratio. Tilt-drive shaft 59 extends through the hollow of centrifuge shaft 39 and thus rotates about centrifuge axis 41. Tilt-shaft pulley 57 and pinion 61 are rigidly coupled to tilt-drive shaft 59 so that the three rotate together. Pinion 61 is engaged with chemical-processing circuits 15 so that they rotate on a 1:3 ratio with pinion 61 and thus on a 1:1 ratio with tilt-motor shaft 51.

Tilt motor 27 is essentially identical to centrifuge motor 25. It includes a position encoder 63 that permits the orientations of chemical-processing circuits 15 to be tracked to 1000 parts per circle (about ⅓°). Tilt-motor encoder 63 is coupled to controller 23 so that the tilts of chemical-processing circuits 15 relative to the centrifugal force can be controlled precisely.

Inductor 19 includes a cable 71 wound on a spool. Cable 81 is coupled to an alternating current source with an adjustable frequency from 10 khz to 1 MHz. Cable 71 serves as a primary winding that is transformer coupled to a coil 73 that includes a gap 75. Coil 73 is a copper laminate structure. AC excitation of coil 73 generates alternating magnetic field to be generated in gap 75. This alternating magnetic field induces eddy currents in metal that is disposed in gap 75.

Each chemical-processing circuit 15 includes three processing stations 81, 82, and 83 coupled by channels 85. During centrifuging, sample tends to accumulate in the radially outward station. Movement of sample from one station to another can be effected by rotating the chemical-processing circuit so that the succeeding station is radially outward ("down" in the supergravity field associated with the centrifugal force). Specifically, this relative orientation determines which station is "outward"; the outward station in general holds the sample.

Chemical-processing circuits 15 each include a base 87 and a cover 88 (not all covers are shown). These ate made of transparent acrylic. Circular bases 87 and covers 88 have 6 cm diameters. Covers 88 are 1 mm thick, while bases have a maximum 3 mm thickness with 2 mm deep molded stations 81, 82, and 83 and channels 85. These leave a 3 cm center barrier 91 that defines radially inward walls for channels 85 and stations 81, 82, and 83. The outer walls of stations 81, 82, and 83 are formed as arcs with 2 cm radii and centers 3.5 cm from the centers of chemical-processing circuits 15.

One stainless steel receptor 93 is loosely fitted in each station 15. Receptors 93 conform to the station shape, but have smaller dimensions than the stations. The receptor thickness is 1 mm. When inductor 19 generates an alternating magnetic field while a receptor 93 is in its gap 75, the receptor heats. The amount of heating is determined by the amount of time the alternating magnetic field is generated while the receptor 93 is in gap 75.

A thermo sensor 95 is formed on the bottom of each receptor 93. Sensor 95 includes an elongated strip that of material that changes color and reflectance when heated. The length of the strip that changes color depends indicates the receptor temperature. This technology is used in Duracell batteries with "PowerCheck™ available from Duracell USA, a division of Duracell, Inc., Berkshire Corporate Park, Bethel, Conn. 06801.

Optical reader 21 is arranged to read thermo-sensors 95. Optical reader 21 includes a Xenon flash lamp 96, lens 97, lens 98, and a photo-diode 99. Controller 23 triggers Xenon flash lamp 96 when, based on motor orientation inputs, a receptor 93 is aligned with reader 21. Lens 97 collimates the resulting flash; lens 98 causes the reflection to converge at photo-diode 99. Photodiode 99 provides an output signal corresponding to the intensity of incident light, which in turn corresponds to the length of sensor 95 that has changed color. Alternatively, an array (e.g., photo-diode or CCD) can be used as the optical reader to provide an image of the sensor. In that case, CCD-pixels corresponding to the heated length of the sensor can be counted to provide a temperature indication.

In system AP1, receptors 15 have identical thermo-sensors 95. Alternatively, thermo-sensors with different ranges can be used depending on the target temperature for the associated station. This reduces the dynamic range required of the sensors and permit greater precision in controlling temperature. Alternatively, more sophisticated sensors can be used to provide range and precision. At one extreme, digital readout thermometers can be included in the receptors. An imaging optical reader with optical-character recognition (OCR) capabilities can be used to monitor sample temperature.

Figure 3:
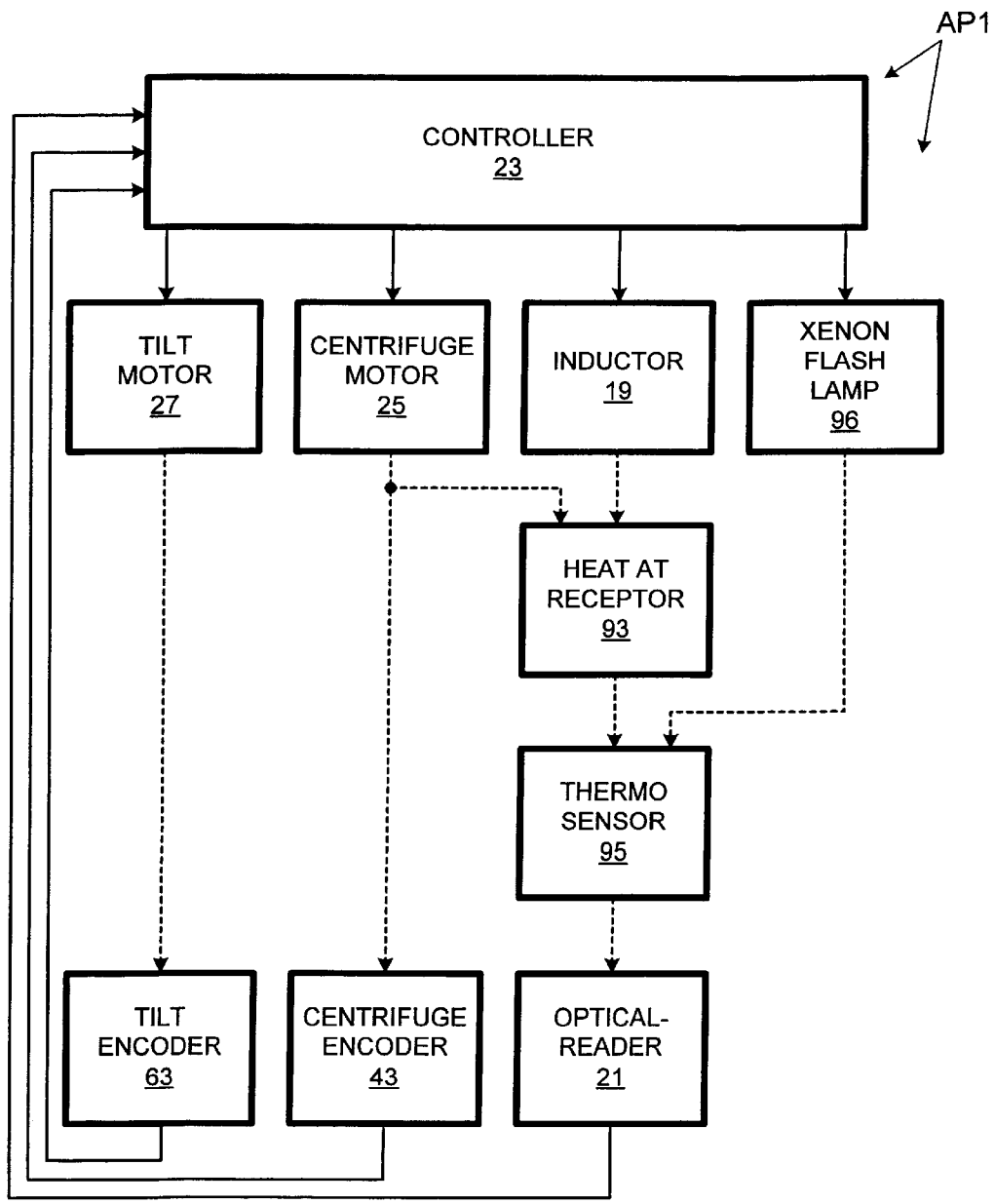
FIG. 3 is a block diagram of the centrifuge system of FIG. 1.

Signal flow for system AP1 is shown in FIG. 3. Controller 23 controls centrifuge motor 25 and tilt motor 27, and thus the centrifuge rotation rate and the orientation of each chemical-processing circuit relative to the centrifugal force.

Centrifuge-motor encoder 43 monitors the orientation of centrifuge motor shaft 39 and, indirectly, the orientation of centrifuge rotor 11. The actual orientation of centrifuge motor shaft 25 can be compared to the intended orientation; any error can be used to adjust the centrifuge rotation rate. Likewise, tilt-motor encoder 63 monitors the orientation of tilt-motor shaft 51 and, indirectly, the orientation of each chemcial-processing circuit 15 relative to the local centrifugal force. Controller 23 controls the spin rates of motors 25 and 27 to minimize deviations from expected centrifuge rates and tilts.

Controller 23 also uses the orientation information to determine when a station 81, 82, 83 is within inductor gap 75, and thus when to fire inductor 19 if additional heating is required. If a temperature increase is required, inductor 19 generates an alternating magnetic field so that eddy currents yield heat in the receptor in gap 75. The temperature of the receptor 93 is continuously indicated by the thermo-sensor 95 on each receptor 93.

Since controller 23 knows the orientation of centrifuge rotor 11, it knows when a thermo-sensor 95 is aligned with optical reader 21, and thus when to fire Xenon flash lamp 96 to get a sample-temperature reading. The resulting reading is provided to controller 23. Controller 23 coordinates the temperature reading with centrifuge orientation information to determine which chemical-processing circuit 15 is involved; controller 23 coordinates the temperature reading and centrifuge orientation with the tilt information to determine which station 81, 82, 83 is involved.

The actual temperature information for a given chemcial-processing station 81, 82, 83 is compared with a target temperature; if the actual temperature falls below the target temperature, controller 23 fires inductor when next the station is in gap 75. The length of time inductor 19 is activated can be adjusted to determine the amount of energy supplied for heating per cycle of rotor 11.

Figure 4:
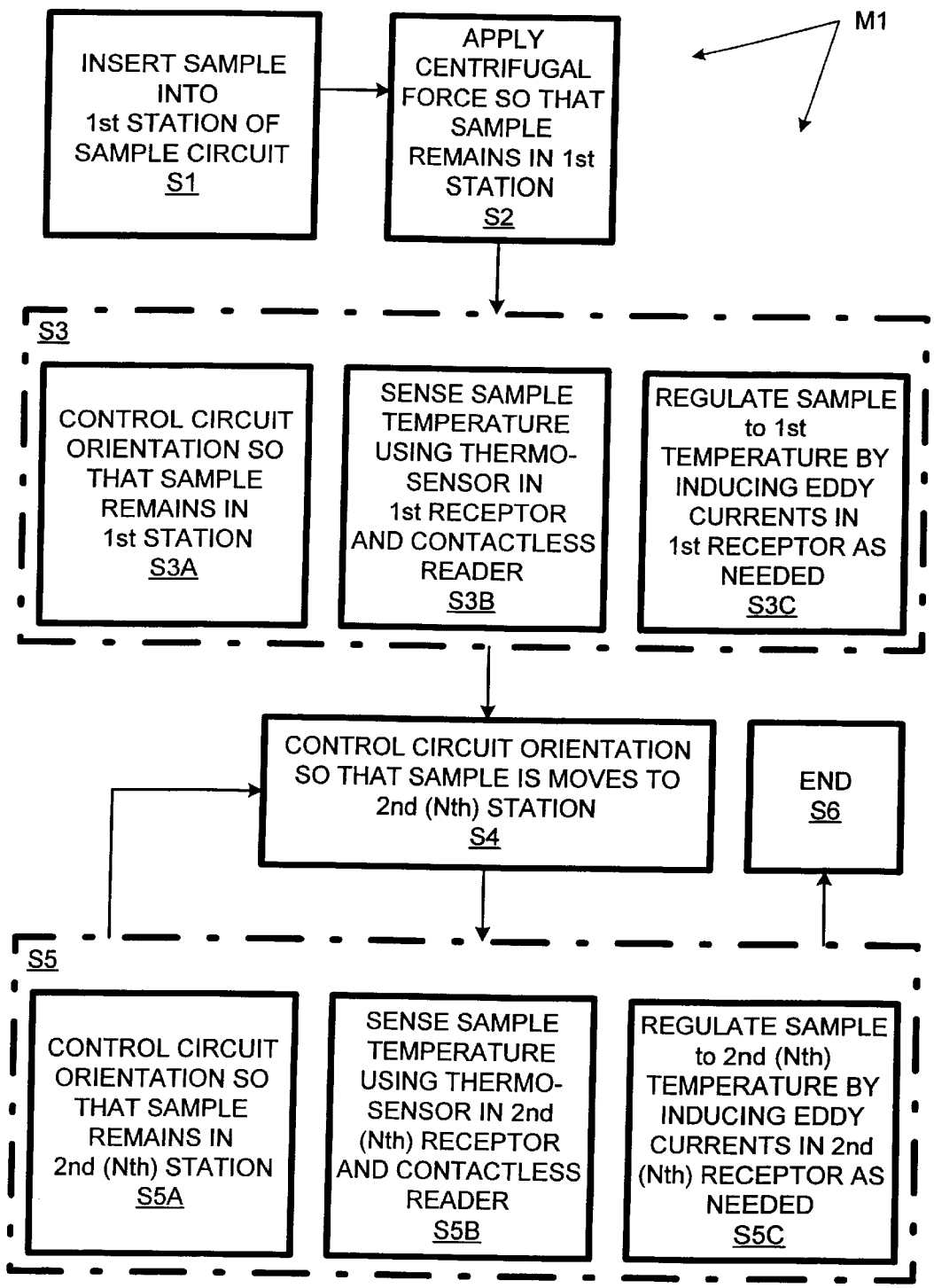
FIG. 4 is a flow chart of a method of the invention practiced in the context of the centrifuge system of FIG. 1.

A method M1 of the invention practiced in the context of system AP1 is flow-charted in FIG. 4. At step S1, sample is inserted into a chemical-processing circuit 15. More specifically, sample is injected via a syringe through a membrane-covered via 101 of the cover of chemical-processing circuit 15. The membrane serves as a septa, sealing the sample circuit interior once the syringe is removed. Via 101 is located over a radially inward portion of the first station 71 that is not contacted by sample during centrifuging. (Each chemical-processing circuit 15 can also have a well for collecting sample upon completion of processing to facilitate sample removal.)

At step S2, centrifuging is begun. Controller 23 activates centrifuge motor 25. 3000 rpm is a typical centrifuge spin rate; it achieves a centrifugal force of 1000 G at 10 cm from the centrifuge axis 41. In general, step S2 is begun with first station 81 down in the centrifugal force field so that the sample remains in the first station 81.

The first sample treatment is conducted at step S3, which includes three generally concurrent substeps S3A, S3B, and S3C. Substep S3A involves controlling sample-circuit orientation so that the sample remains in the first station 71. This can mean rotating the chemcial-processing circuit 15 at the centrifuge rate so that its orientation relative to centrifuge rotor 11 does not change. However, if some agitation is required, the tilt rate can oscillate above and below the centrifuge rate.

Substep S3B involves sensing sample temperature using thermo-sensors 95 built into receptors 93, and contactless reading of thermo-sensors 95 using optical reader 21. Readings can be taken of each chemcial-processing circuit 15 as it passes reader 21. However, to accommodate charge-time requirements for Xenon flash lamp 96, readings do not need to occur every pass of every circuit. Likewise, if a CCD-ased reader is used, readings can be spaced to allow time for CCD data to be read out and processed.

Substep S3C involves regulating sample temperature to a first temperature using the readings obtained in substep S3B. If a reading indicates the sample temperature is below the target first temperature, controller 23 controls inductor 19 so that it generates eddy currents in the appropriate receptor 93 when that receptor is in the inductor gap 75. The length of time the eddy currents are induced can be adjusted to correspond to the magnitude of the temperature deviation. The first temperature need not be a constant; the temperature can be regulated to match a desired temperature-versus-time function.

Step S3 continues until the first sample treatment is completed. Step S4 involves changing circuit orientation relative to the centrifugal force so that the sample is urged through an inter-station channel 85 to the second station 82. Step S5 parallels step S3, and has the corresponding substeps S5A, S5B, and S5C.

If more than two treatments are required, step S5 can be iterated, in which case, reference is to an Nth station, an Nth receptor, and an Nth temperature. Note that the Nth station can be the same as an earlier station. In the illustrated case, the third station is different from the second and first stations, but the fourth station would be the same as the first station and the fifth station would be the same as the sixth station, and so on. Once processing is complete, method M1 ends at step S6.

In the context of PCR, the sample can be a DNA fragment. The three stations 81, 82, 83 can be heated respectively to 90° C., 60° C. and 70° C. The DNA sample can be introduced into first station 81 and the centrifuge accelerated to 3000 rpm. Chemical-processing circuit 15 can be rocked back and forth +/1 6d at 5 Hz to facilitate rapid and uniform heating of the DNA sample solution. Melting is likely to be complete by the time the full centrifuge rate is achieved.

The orientation of chemical-processing circuit 15 can be changed 120° so that the DNA sample pours into second station 82, which is maintained at 60° C. Chemical-processing circuit 15 can be rocked back and forth to agitate the DNA sample so that the new temperature is achieved uniformly and rapidly. Once the annealing step is complete, chemical-processing circuit 15 can be reoriented so that the DNA sample pours into station 83, which is at 70° C., optimized for the extension reaction. Again, chemical-processing circuit 15 can be agitated to facilitate a rapid and uniform temperature change. Once the extension reaction is complete, chemical-processing circuit 15 can be reoriented so that the DNA sample pours into first station 81, to begin the next iteration of the PCR procedure.

The present invention has industrial applicability in any field where chemical processes can take advantages of supergravity conditions offered by a centrifuge. A wide variety of chemical processing sequences can be accommodated using different chemical-processing circuit designs. The illustrated chemical-processing circuits 15 have three stations 81, 82, and 83 arranged in a closed loop for automated three-step PCR procedures. Alternatively, there can be two stations or more than three. The stations can be arranged in a closed loop or in an open loop. An open loop can be suited for non-iterated procedures in which a return to a first station is not needed or desired. These and other variations upon and modifications to the described embodiments are provided by the present invention, the scope of which is defined by the following claims.

What is claimed is:

1. A centrifuge system comprising:

a rotor;

a centrifuge drive for rotating said rotor about a centrifuge axis;

a chemical-processing unit for containing a chemical sample, said chemical-processing unit having a receptor that dissipates heat when eddy currents are induced therein, said chemical-processing unit being coupled so said rotor so that centrifugal force is applied thereto when said rotor rotates;

an inductor for inducing said eddy currents in said receptor as said rotor is rotating;

centrifuge-orientation indicating means for indicating the orientation of said rotor; and a controller coupled to said centrifuge-orientation indicating means and said inductor, said inductor inducing said eddy currents by generating an alternating magnetic field, said controller controlling said inductor so that it generates said alternating magnetic field only at times determined at least in part as a function of the orientation of said rotor.

2. A centrifuge system as recited in claim 1 further comprising a tilt drive for controlling the orientation of said chemical-processing unit relative to said rotor, said tilt drive including a motor mechanically coupled to said chemical-processing unit.

3. A centrifuge system as recited in claim 1 wherein said chemical-processing unit includes a temperature sensor that provides an optical indication of a receptor temperature associated with said chemical-processing unit.

4. A centrifuge system as recited in claim 3 further comprising an optical reader for providing a temperature indication of said receptor temperature to said controller by optically reading said optical indication.

5. A centrifuge system as recited in claim 4 wherein said controller regulates said receptor temperature so that it is maintained at a predetermined temperature, said predetermined temperature being at least in part a function of the orientation of said chemical-processing unit relative to said rotor.

6. A centrifuge system as recited in claim 1 wherein said chemical-processing unit has first and second chemical-processing stations, said controller moving said chemical sample from said first chemical-processing station to said second chemical-processing station by changing the orientation of said chemical-processing unit relative to said rotor.

7. A method comprising:

spinning a chemical-processing unit containing a chemical sample about a centrifuge axis of a centrifuge rotor so as to subject said chemical sample to a centrifugal force; and heating said chemical sample by inducing eddy currents in said chemical-processing unit using an inductor not subject to said centrifugal force, said inductor inducing said eddy currents by generating an alternating magnetic field, said inductor generating said alternating magnetic field only at times determined as a function of the orientation of said centrifuge rotor.

8. A method as recited in claim 7 further comprising: controlling the orientation of said chemical-processing unit relative to said centrifugal force using a motor mechanically coupled to said chemical-processing unit so as to move said chemical sample within said chemical-processing unit during said heating and said spinning.

9. A method as recited in claim 7 further comprising monitoring an actual temperature associated with said chemical-processing unit by using a reader not subject to said centrifugal force to contactlessly read a thermo-sensor of said chemical-processing unit and subject to said centrifugal force.

10. A method as recited in claim 7 wherein said controlling step involves moving said chemical sample from a first station of said chemical-processing unit to a second station of said chemical processing unit.

11. A method as recited in claim 10 further comprising monitoring an actual temperature associated with said chemical-processing unit by using a reader not subject to said centrifugal force to contactlessly read a first thermo-sensor of said chemical-processing unit associated with said first station while said chemical sample is at said first station and to contactlessly read a second thermo-sensor of said chemical-processing unit associated with said second station while said chemical sample is at said second station.

12. A method as recited in claim 11 wherein said inductor induces said eddy currents by generating an alternating magnetic field, said inductor generating said alternating magnetic field only at times determined as a function of the orientation of said centrifuge rotor, while said sample is at said first station, said inductor generates said alternating magnetic field at times when said first thermo-sensor indicates an actual temperature below a first target temperature, and while said sample is at said second station, said inductor generates said alternating magnetic field at times when said second thermo-sensor indicates an actual temperature below a second target temperature different from said first target temperature.

13. A method of automating a series of sample treatments including a first treatment to be conducted at a first temperature and a second treatment to conducted at a second temperature different from said first temperature, said method comprising the steps of:

inserting a sample into a chemical-processing circuit with a first treatment station and a second treatment station, said chemical-processing circuit being designed so that said sample can be moved from said first treatment station to said second treatment station by controlling the orientation of said chemical-processing circuit relative to a centrifugal force;

applying said centrifugal force through the following steps;

while said sample is in said first treatment station,
orienting said chemical-processing circuit so that said sample remains in said first treatment station,
sensing the temperature of said sample using a first sensor included in said chemical-processing circuit; and
regulating said temperature to maintain it at said first temperature by inducing eddy currents as needed in said chemical-processing circuit;

controlling the orientation of said chemical-processing circuit relative to said centrifugal force so that said sample moves from said first treatment station to said second treatment station; and while said sample is in said second treatment location,
orienting said chemical-processing circuit so that said sample remains in said second treatment station, sensing the temperature of said sample using a second sensor included in said chemical-processing circuit; and regulating said temperature to maintain it at said second temperature by inducing eddy currents as needed in said chemical-processing circuit.

14. A method as recited in claim 13 further comprising optically reading temperature indications from said sensor and using the resulting readings in regulating said temperature.

15. A method as recited in claim 14 wherein said eddy currents are induced by an inductor that generates an alternating magnetic field.

16. A method as recited in claim 15 wherein said inductor generates said alternating magnetic fields only at times determined by the orientation of said chemical-processing circuit relative to a centrifuge axis.

* * * * *